(12) United States Patent
Sun

(10) Patent No.: US 12,186,104 B2
(45) Date of Patent: Jan. 7, 2025

(54) SYSTEMS AND METHODS FOR CORRECTING INTRAVOXEL AND/OR VOXEL INHOMOGENEITY

(71) Applicant: Emory University, Atlanta, GA (US)

(72) Inventor: Phillip Zhe Sun, Atlanta, GA (US)

(73) Assignee: Emory University, Atlanta, GA (US)

( * ) Notice: Subject to any disclaimer, the term of this patent is extended or adjusted under 35 U.S.C. 154(b) by 316 days.

(21) Appl. No.: 17/639,276

(22) PCT Filed: Jun. 30, 2020

(86) PCT No.: PCT/US2020/040216
§ 371 (c)(1),
(2) Date: Feb. 28, 2022

(87) PCT Pub. No.: WO2021/040880
PCT Pub. Date: Mar. 4, 2021

(65) Prior Publication Data
US 2022/0342021 A1     Oct. 27, 2022

Related U.S. Application Data

(60) Provisional application No. 62/894,563, filed on Aug. 30, 2019.

(51) Int. Cl.
*G01R 33/56* (2006.01)
*A61B 5/00* (2006.01)
(Continued)

(52) U.S. Cl.
CPC .......... *A61B 5/7203* (2013.01); *G01R 33/445* (2013.01); *G01R 33/483* (2013.01);
(Continued)

(58) Field of Classification Search
CPC .... A61B 5/7203; A61B 5/055; G01R 33/445; G01R 33/483; G01R 33/5605;
(Continued)

(56) References Cited

U.S. PATENT DOCUMENTS 6,943,033 B2    9/2005  Van Zijl et al.
7,782,056 B2 *  8/2010  Noterdaeme .... G01R 33/56563
                                                    324/309
(Continued)

FOREIGN PATENT DOCUMENTS

EP          3511729 A1      7/2019
WO    WO 2016186644 A1     11/2016
WO    WO 2019067615 A1      4/2019

OTHER PUBLICATIONS

Kim, Jinsuh, et al. "A review of optimization and quantification techniques for chemical exchange saturation transfer MRI toward sensitive in vivo imaging." Contrast media & molecular imaging 10.3 (2015): 163-178. (Year: 2015).*

(Continued)

*Primary Examiner* — Edward F Urban
*Assistant Examiner* — Jongbong Nah
(74) *Attorney, Agent, or Firm* — Emory Patent Group

(57) ABSTRACT

The devices, systems, and methods can improve magnetic resonance imaging (MRI), MR spectroscopy (MRS), MR spectroscopic imaging (MRSI) measurement(s), thereby providing more reliable quantification. The method may include a method for correcting MR image(s)/spectrum. The method may include providing an inhomogeneity field/response map of a region of interest; and providing MR image(s)/spectrum of the region of interest. The method may include determining an intravoxel/voxel inhomogeneity correction coefficient for each voxel of at least one subregion of the region of the interest using the inhomogeneity field/response map. The method may include correcting each voxel of the MR image(s)/spectrum of the region of interest using the intravoxel/voxel inhomogeneity correction coefficient. The MR image(s)/spectrum may include chemical exchange saturation transfer (CEST)/magnetization transfer (Continued)

(MT) imaging with Z-spectrum, CEST/MT imaging without Z-spectrum, CEST spectroscopy, CEST MRS, MRS, MRSI, or any combination thereof.

19 Claims, 14 Drawing Sheets

(51) Int. Cl.
  *G01R 33/44* (2006.01)
  *G01R 33/483* (2006.01)
  *G06V 10/25* (2022.01)
  *G06V 10/98* (2022.01)

(52) U.S. Cl.
  CPC ..... *G01R 33/5605* (2013.01); *G01R 33/5608* (2013.01); *G06V 10/25* (2022.01); *G06V 10/98* (2022.01)

(58) Field of Classification Search
  CPC .............. G01R 33/5608; G01R 33/243; G01R 33/56563; G06V 10/25; G06V 10/98
  See application file for complete search history.

(56) References Cited

U.S. PATENT DOCUMENTS

| | | | |
|---|---|---|---|
| 8,278,925 B2 | 10/2012 | Sun et al. | |
| 8,872,515 B2 | 10/2014 | Sun | |
| 8,928,317 B2 | 1/2015 | Sun | |
| 9,547,058 B2 | 1/2017 | Miyazaki et al. | |
| 9,824,448 B2 | 11/2017 | Liu et al. | |
| 10,001,536 B2 | 6/2018 | Sun | |
| 10,018,700 B2* | 7/2018 | Alhamud | G01R 33/4828 |
| 10,078,123 B2 | 9/2018 | Sun | |
| 10,191,134 B2 | 1/2019 | Pfeuffer et al. | |
| 2010/0085050 A1* | 4/2010 | Dong | G01R 33/485 324/309 |
| 2015/0338483 A1 | 11/2015 | Sun | |
| 2016/0124065 A1* | 5/2016 | Pfeuffer | G01R 33/56563 324/309 |
| 2018/0268546 A1 | 9/2018 | Sun et al. | |
| 2018/0292495 A1 | 10/2018 | Sun | |
| 2019/0011516 A1* | 1/2019 | Sun | G01R 33/4838 |
| 2021/0063519 A1* | 3/2021 | Keupp | G01R 33/5608 |

OTHER PUBLICATIONS

Dong, Zhengchao, and Bradley S. Peterson. "Spectral resolution amelioration by deconvolution (SPREAD) in MR spectroscopic imaging." Journal of Magnetic Resonance Imaging: An Official Journal of the International Society for Magnetic Resonance in Medicine 29.6 (2009): 1395-1405. (Year: 2009).*

Dong et al. "Spectral Resolution Amelioration by Deconvolution (SPREAD) in MR Spectroscopic Imaging." Journal of Magnetic Resonance Imaging, 2009; 29:1395-1405.

Kim et al. "Water Saturation Shift Referencing (WASSR) for Chemical Exchange Saturation Transfer (CEST) Experiments." Magnetic Resonance in Medicine, 2009; 61:1441-1450.

Kim et al. "A review of optimization and quantification techniques for chemical exchange saturation transfer (CEST) MRI toward sensitive in vivo imaging." Contrast Media & Molecular Imaging, 2015; 10(3):163-178.

Sun et al. "Development of intravoxel inhomogeneity correction for chemical exchange saturation transfer (CEST) spectral imaging: a high-resolution field map-based deconvolution algorithm for magnetic field inhomogeneity correction." Magnetic Resonance in Medicine, 2020; 83(4):1348-1355.

Zhang et al. "Quasi-steady-state (QUASS) CEST for robust quantification of tumor MT and APT effects by correction of saturation time and relaxation delay." 2021 ISMRM & SMRT Annual Meeting & Exhibition, May 15-20, 2021; Abstract #0149.

Extended European Search Report for EP Application No. 20858705.5 dated Jul. 26, 2023.

International Search Report and Written Opinion for PCT Application No. PCT/US2020/040216 dated Jun. 30, 2020.

* cited by examiner

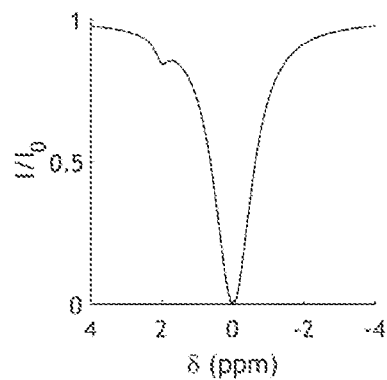 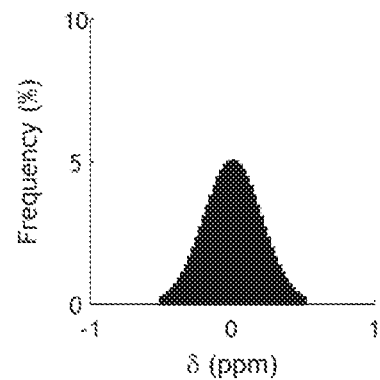
FIG. 4A
FIG. 4B
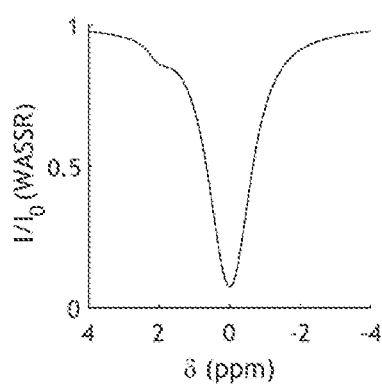 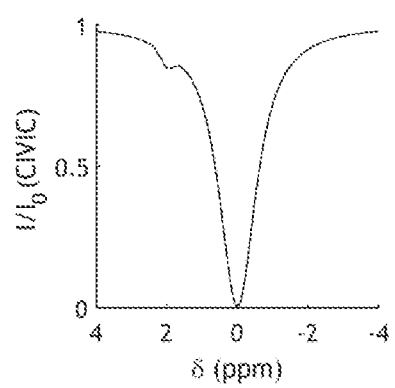
FIG. 4C
FIG. 4D

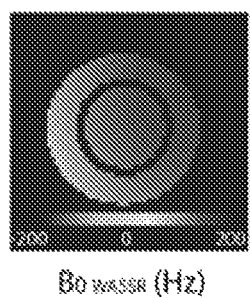 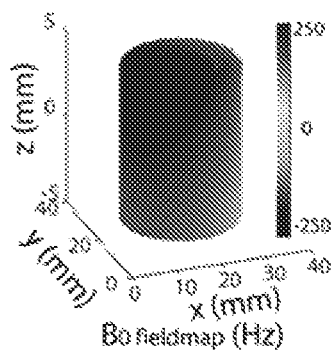 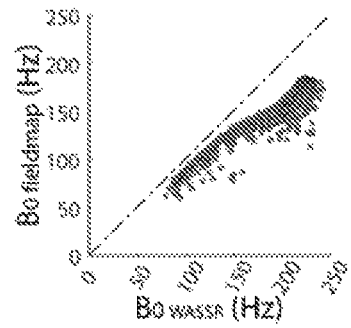
FIG. 5A  FIG. 5B  FIG. 5C
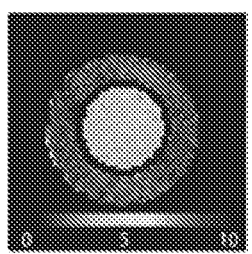 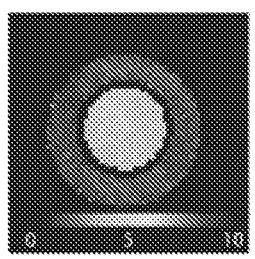 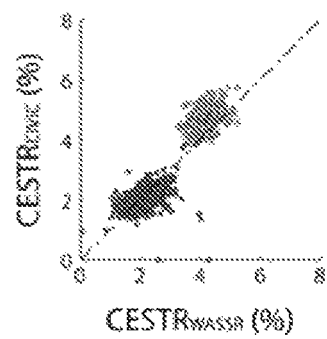
FIG. 5D  FIG. 5E  FIG. 5F
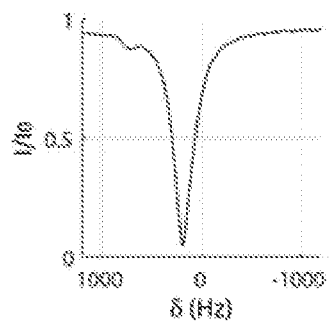 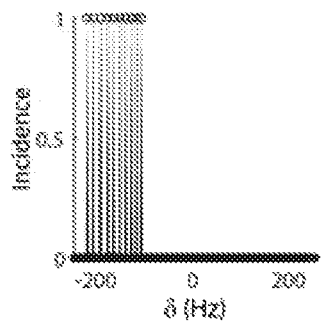 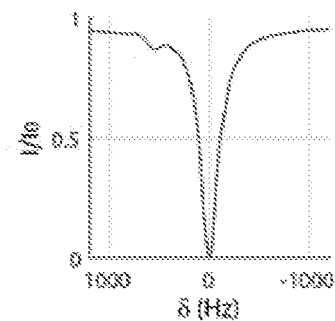
FIG. 6A  FIG. 6B  FIG. 6C

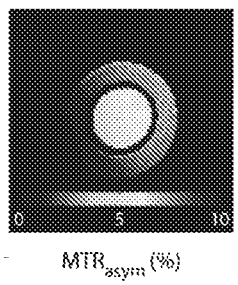 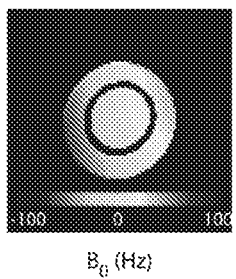 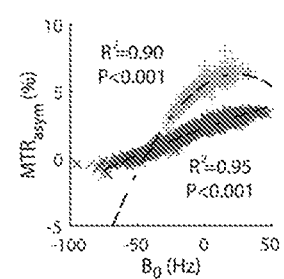
FIG. 11A    FIG. 11B    FIG. 11C
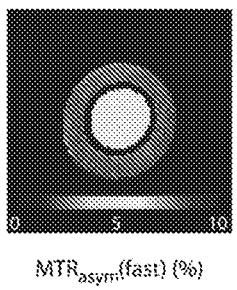 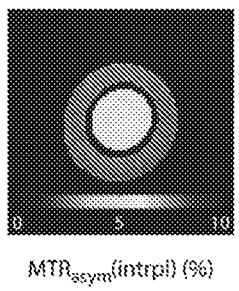 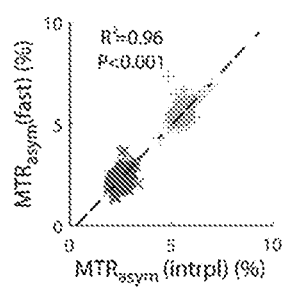
FIG. 11D    FIG. 11E    FIG. 11F
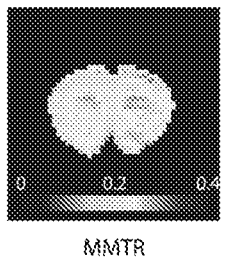 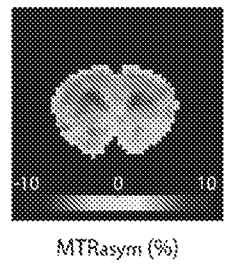 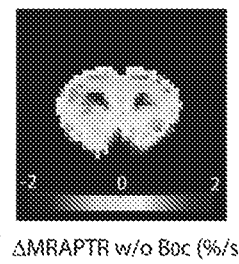 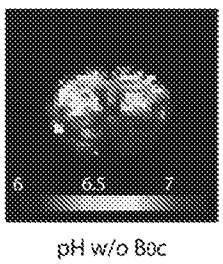
FIG. 12A    FIG. 12B    FIG. 12C    FIG. 12D
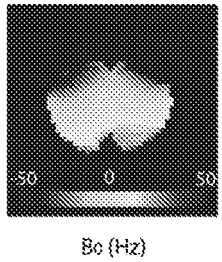 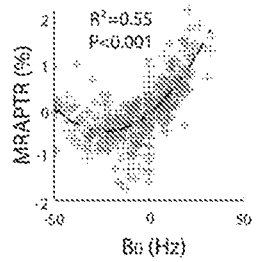 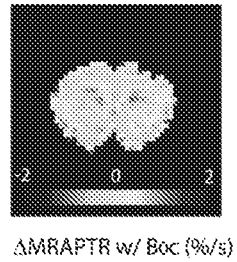 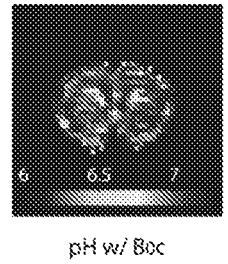
FIG. 12E    FIG. 12F    FIG. 12G    FIG. 12H

SYSTEMS AND METHODS FOR CORRECTING INTRAVOXEL AND/OR VOXEL INHOMOGENEITY

This application is the National Stage of International Application No. PCT/US2020/040216 filed Jun. 30, 2020, which claims the benefit of U.S. Provisional Application No. 62/894,563 filed Aug. 30, 2019. The entirety of each of these applications is hereby incorporated by reference for all purposes.

STATEMENT REGARDING FEDERALLY SPONSORED RESEARCH OR DEVELOPMENT

This invention was made with government support under NS083654 and AR071529 awarded by the National Institutes of Health. The government has certain rights in the invention.

BACKGROUND

Magnetic resonance (MR) imaging and spectroscopic techniques are commonly used in clinical and research applications. There have been recent advances to address the low sensitivity limitations of MR imaging, such as in vivo imaging at high fields and new imaging techniques (e.g., chemical exchange saturation transfer (CEST) MR imaging, MR spectroscopy (MRS), and MR spectroscopy imaging (MRSI)). However, these advanced MR imaging techniques can be susceptible to distortions, such as field inhomogeneity, particularly, $B_0$ field inhomogeneity, resulting in unreliable and/or inaccurate quantitative MR images. Further, commonly used field inhomogeneity correction techniques can be time-consuming and challenging to be performed in vivo.

SUMMARY

Thus, there is a need for accurate and efficient techniques that can correct for field inhomogeneity-induced measurement errors resulting in more reliable and accurate quantitative MR imaging, such as chemical exchange saturation transfer (CEST) MR imaging, magnetization transfer (MT) imaging, MR spectroscopy (MRS), and/or MR spectroscopy imaging (MRSI). Additionally, there is a need for accurate and efficient techniques that can standardize for different scanning parameters, including saturation time and relaxation delay.

The devices, systems, and methods can improve and/or standardize CEST/MT MRI, MRS and MRSI measurement, thereby providing more reliable quantification.

In some embodiments, the methods may include a method for correcting MR image(s)/spectrum. The method may include providing an inhomogeneity field/response map of a region of interest; and providing MR image(s)/spectrum of a region of interest. The method may include determining an intravoxel inhomogeneity correction coefficient for each voxel of at least one subregion of the region of the interest using the inhomogeneity field/response map. The method may further include correcting each voxel of the MR image(s)/spectrum of the region of interest using the intravoxel/voxel inhomogeneity correction coefficient.

The MR image(s)/spectrum may include CEST or MT imaging with Z-spectrum, CEST or MT imaging without Z-spectrum, CEST spectroscopy, MRS, MRSI, or any combination thereof.

In some embodiments, the methods may include a method for standardizing MR images/spectrum. In some embodiments, the method may include providing MR images/spectrum corrected for intravoxel inhomogeneity. The corrected MR images/spectrum may include a plurality of corrected voxels. In some embodiments, the method may include determining a quasi-steady state signal for each corrected voxel for each saturation offset using T1 map, B1, and scan parameters. In some embodiments, the methods may include standardizing each corrected voxel using the quasi-steady state signal for each saturation offset. In some embodiments, the corrected MR image(s)/spectrum may include CEST or MT imaging with Z-spectrum, CEST or MT imaging without Z-spectrum, CEST spectroscopy, CEST MRS or MRSI, or any combination thereof.

In some embodiments, the determining the quasi-steady state spectrum for each voxel may include determining a tilt angle for each voxel using gyromagnetic ratio, amplitude of RF saturation pulse, and offset of the RF saturation. In some embodiments, the gyromagnetic ratio, amplitude of RF saturation pulse and offset of the RF saturation may be determined using the corrected voxel with field inhomogeneity correction. In some embodiments, the method may further include determining a steady state spinlock relaxation rate using the tilt angle. In some embodiments, the method may also include determining the quasi-steady state signal for each voxel for each saturation offset based on the steady state spinlock relaxation rate.

In some embodiments, the methods may include determining one or more quantitative measurements using each standardized and/or corrected voxel. In some embodiments, the one more quantitative measurements may include CEST asymmetry (CESTR) image, the CEST exchange effect ($R_{ex}$), labile proton concentration, labile proton exchange rate, among others, or any combination thereof.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, the emphasis being placed upon illustrating the principles of the disclosure.

FIGS. 4A-D shows an example of the simulation of the high-resolution field map-based inhomogeneity correction method for CEST Z-spectrum according to embodiments. FIG. 4A shows an example of a simulated Z-spectrum without $B_0$ inhomogeneity. FIG. 4B shows an example of a simulated symmetric $B_0$ inhomogeneity dispersion within a single CEST MRI voxel or ROI. FIG. 4C shows the apparent Z-spectrum in the presence of symmetric $B_0$ inhomogeneity dispersion. FIG. 4D shows the original Z spectrum that has been recovered and is in agreement with FIG. 4A using the method 300 according to embodiments;

FIGS. 5A-F show another example of the application of the high-resolution field map-based inhomogeneity correction method for CEST Z-spectral imaging according to embodiments. FIG. 5A shows another example of a $B_0$ field inhomogeneity map determined from water saturation shift referencing (WASSR) approach. FIG. 5B shows an example of a high-resolution $B_0$ field inhomogeneity map. FIG. 5C shows that the correlation between per-pixel $B_0$ field inhomogeneity (FIG. 5A) and averaged subvoxel $B_0$ field inhomogeneity (FIG. 5B) per pixel. FIGS. 5D and 5E show CEST images ($MTR_{asym}$) obtained from conventional interpolation correction and the CIVIC correction, respectively. FIG. 5F shows the correlation of the corrections shown in FIGS. 5D and 5E;

FIGS. 6A-C show another example of the application of the high-resolution field map-based inhomogeneity correction method for CEST Z-spectral imaging according to embodiments. FIG. 6A shows an example of a Z spectrum from a single voxel. FIG. 6B shows the subvoxel $B_0$ field inhomogeneity for the pixel shown in FIG. 6A. FIG. 6C shows the reconstructed Z-spectrum after correction using the subvoxel inhomogeneity correction coefficient according to the method 300 according to embodiments;

FIGS. 11A-F show an example of the application of the field map-based voxel inhomogeneity correction method for CEST imaging without the need of Z-spectrum. FIG. 11A shows an example of raw MTR asymmetry ($MTR_{asym}$) image calculated from an asymmetry analysis, with noticeable $B_0$ inhomogeneity artifact. FIG. 11B shows the $B_0$ inhomogeneity map determined from the WASSR scan. FIG. 11C shows a regression analysis between $B_0$ inhomogeneity and raw $MTR_{asym}$, per pixel for each ROI (interior and exterior compartment). FIG. 11D shows the fast $B_0$ inhomogeneity-corrected $MTR_{asym}$(fast) map. FIG. 11E shows the interpolation-based $B_0$ inhomogeneity-corrected $MTR_{asym}$ (intrpl) map. FIG. 11F shows the regression analysis between $MTR_{asym}$ (fast) and $MTR_{asym}$ (intrpl), per pixel;

FIGS. 12A-H show another example of the application of the field map-based voxel inhomogeneity correction method for CEST imaging without the need of Z-spectrum. FIG. 12A shows an example of an acquired mean magnetization transfer ratio (MMTR) at ±3.5 ppm. FIG. 12B shows an example of an acquired pH-sensitive $MTR_{asym}$ map. FIG. 12C shows pH-specific ΔMRAPTR map without $B_0$ inhomogeneity correction. FIG. 12D shows a pH map determined from ΔMRAPTR map without $B_0$ inhomogeneity correction. FIG. 12E shows $B_0$ inhomogeneity map determined from the WASSR scan is shown in FIG. 12E. FIG. 12F shows the regression analysis between $B_0$ inhomogeneity and raw ΔMRAPTR, per pixel. FIG. 12G shows ΔMRAPTR map with the proposed fast $B_0$ inhomogeneity correction. FIG. 12H shows the corresponding pH map with the proposed fast $B_0$ inhomogeneity correction;

FIG. 14A shows three representative apparent Z-spectra with Td/Ts=1 s/1 s (x markers), Td/Ts=3 s/3 s (diamond markers), Td/Ts=10 s/10 s (+ markers). FIG. 14B shows the corresponding apparent Z-spectral asymmetry from the three representative saturation time and relaxation delay. FIG. 14C shows the apparent CEST effect at 2 ppm as a function of the saturation time and relaxation delay;

FIG. 15A shows a comparison of the apparent R1ρ spectra (without correction) obtained under long saturation duration and relaxation delay of Td/Ts=10 s/10 s (+ markers in black), and the corrected R1ρ from the quasi-steady state solution under Td/Ts=1 s/1 s (x markers), Td/Ts=3 s/3 s (diamond markers), Td/Ts=10 s/10 s (+ markers in gray). FIG. 15B shows the Z-spectra from the quasi-steady state solution for Td/Ts=1 s/1 s (x markers), Td/Ts=3 s/3 s (diamond markers), Td/Ts=10 s/10 s (+ markers in gray) and the long saturation time and relaxation delay (Td/Ts=10 s/10 s, + markers in black). FIG. 15C shows asymmetry Z-spectra from the quasi-steady state solution for Td/Ts=1 s/1 s (x markers), Td/Ts=3 s/3 s (diamond markers), Td/Ts=10 s/10 s (+ markers in gray) and that under long saturation time and relaxation delay (Td/Ts=10 s/10 s, + markers in black). FIG. 15D shows the CEST effect calculated from the quasi-steady state solution as function of Ts and Td;

FIG. 16A shows an example of the normalized exchange rate determined from the omega plot of the apparent CEST effect as a function of Td and Ts. FIG. 16B shows an example of the normalized labile proton concentration determined from the omega plot of the apparent CEST effect, as a function of Td and Ts. FIG. 16C shows an example of the normalized labile proton exchange rate determined using the standardization method according to embodiments. FIG. 16D shows an example of the ratio determined using the standardization method according to embodiments.

DESCRIPTION OF THE EMBODIMENTS

Figure 1:
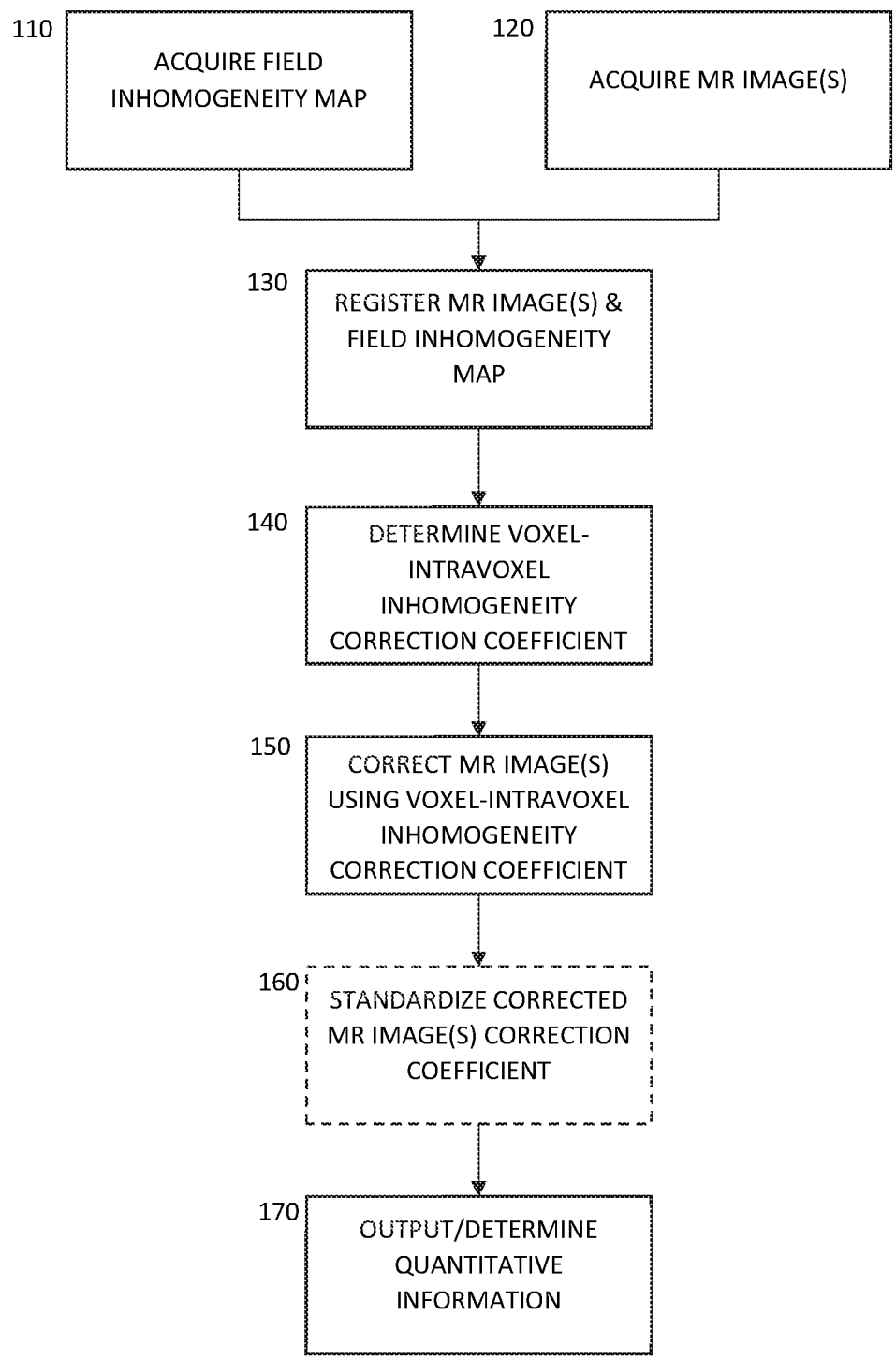
FIG. 1 shows an example of a high-resolution field/response map based inhomogeneity correction method for MR image(s)/spectrum according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems and methods of the disclosure can provide high-resolution field/response map based intravoxel and/or voxel inhomogeneity correction for MR imaging, including chemical exchange saturation transfer (CEST) imaging, CEST spectroscopy, magnetization transfer (MT), MR image(s), MR spectroscopy (MRS) MR spectroscopic imaging (MRSI), or any combination thereof. In some examples, the systems and methods of the disclosure do not assume negligible intravoxel field inhomogeneity, such as routine $B_0$ field correction methods, and thus by generating an intravoxel correction coefficient, the systems and methods can identify and correct regions of non-negligible intravoxel field heterogeneity. Thus, the intravoxel inhomogeneity correction according to the disclosure can improve the CEST MRI and spectroscopy contrast and/or contrast to noise ratio (CNR), thereby improving the efficiency and accuracy of MR imaging, such as MM, MRS, and MRSI.

In some embodiments, the subvoxel inhomogeneity correction can be determined using a complete or a segment of Z-spectrum. In some embodiments, the voxel inhomogeneity correction can be performed without requiring the acquisition of the Z-spectral, thereby reducing the scan time. This can be beneficial to implementation in the emergency setting, where it is desired to minimize the imaging time for a timely intervention.

While some example of the disclosure may be specific to the brain, it will be understood that these example are nonlimiting and that the methods and systems may be performed for other parts of the body, including but not limited to the myocardium, muscle and kidney. Additionally, while some example of the disclosure may be specific to CEST imaging, it will be understood that these examples are also nonlimiting and that the methods and systems may also be applied to other types of MR imaging, including but not limited to MRS and MRSI. Further, while some example of the disclosure may be specific to correcting $B_0$ field map inhomogeneity, it will be understood that these examples are also nonlimiting and that the methods and systems may also be used to correct $B_1$ field map inhomogeneity.

FIG. 1 shows a method 100 of a high-resolution field map-based inhomogeneity correction (CIVIC) method for MR image(s)/spectrum (e.g., CEST, MT, MRS, MRSI, etc.) of a subject by determining and applying an intravoxel inhomogeneity correction coefficient according to embodiments.

In some embodiments, the method 100 may include a step 110 of acquiring an inhomogeneity field/response map (e.g., $B_0$ field inhomogeneity map) and a step 120 of acquiring MR image(s)/spectrum of one or more regions of interest (e.g., a brain) using one or more scans. In the steps 110 and 120, a subject may be arranged in a magnetic resonance (MR) system capable of acquiring MR data/spectra and the data for field (e.g., $B_0$ field) inhomogeneity map. In some embodiments, the data may be acquired simultaneously. The MR system may include any available system and protocol, for example, capable of acquiring MRS/MRSI data, CEST data with and/or without Z-spectrum, field maps, among others, etc.

By way of example, the inhomogeneity field map may be a high-resolution $B_0$ field inhomogeneity map generated using routine $B_0$ field inhomogeneity map data and/or a high-resolution routine $B_0$ field inhomogeneity map data that directly maps the acquired $B_0$ field inhomogeneity map data. The $B_0$ field inhomogeneity map may be acquired and/or generated using any available methods.

The MR image(s)/spectrum may be CEST image(s)/spectrum with and/or without Z-spectrum, MT image(s)/spectrum with and/or without Z-spectrum, MRS/MRSI image(s)/spectrum, among others, or any combination thereof.

In some embodiments, the method 100 may include a step 130 of registering the MR image(s)/spectrum and $B_0$ inhomogeneity field map, for example, using any available method such as Statistical Parametric Mapping (SPM) and Advanced Normalization Tools (ANTs). Using the registered inhomogeneity field map, the method 100 may include a step 140 of determining an intravoxel inhomogeneity correction coefficient for each voxel of the region of interest. For example, the intravoxel inhomogeneity correction coefficient may be determined using a point-spread-function, a regression function, among others, or a combination thereof. The determination of the intravoxel inhomogeneity correction coefficient may be based on the type of data (e.g., CEST or MT with Z-spectrum, CEST or MT without Z-spectrum, MRS/MRSI data, etc.). FIGS. 2A-12 show examples of determining the intravoxel/voxel inhomogeneity correction coefficient for different types of MR data according to embodiments.

Figure 2A:
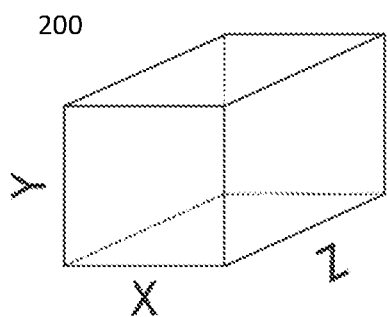
FIG. 2A shows a voxel of the MR image(s)/spectrum and FIG. 2B shows the corresponding subvoxel $B_0$ inhomogeneity field map according to embodiments.
Figure 2B:
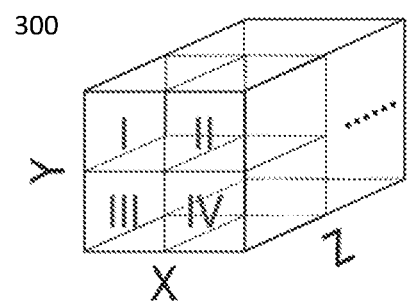

By way of example, FIG. 2A illustrates an example of a voxel 200 of a MR image and FIG. 2B shows the corresponding $B_0$ inhomogeneity field map 300 for which the intravoxel inhomogeneity has been quantified (i.e., corresponding intravoxel inhomogeneity coefficient for the voxel 200). As shown in these figures, each voxel of the MR image corresponds to multiple subvoxels of the $B_0$ inhomogeneity map. In this example, the $B_0$ inhomogeneity field map 300 shown in FIG. 2B has 2×2×n subvoxels for each MR (e.g., CEST or MRS/MRSI) image voxel. It will be understood that the intravoxel inhomogeneity coefficient can be determined for more or fewer subvoxels for each voxel. This subvoxel information can be used to generate the intravoxel inhomogeneity correction coefficient for each voxel.

After the intravoxel inhomogeneity correction coefficient is determined for each voxel of the region of interest, the method 100 may include a step 150 of correcting the MR image(s), MR spectroscopy (MRS) and/or MR spectroscopy imaging using the intravoxel inhomogeneity correction coefficient for each voxel. For example, the CEST MR image(s), magnetization transfer (MT) MR image(s), CEST MR spectroscopy, CEST MR spectroscopy imaging, MR spectroscopy (MRS) and/or MR spectroscopy imaging may be reconstructed using the intravoxel inhomogeneity correction coefficient for each voxel.

In some embodiments, the method 100 may include an optional step 160 of standardizing the corrected MR image(s)/spectrum from the step 150. For example, the corrected MR image(s) spectrum may be standardized by correcting the original Z-spectrum offset by offset, such as saturation or frequency offset. By way of example, the step 160 may include determining a quasi-steady state signal ($I/I_0$) for each voxel/component for each saturation offset. This way, image(s) and related quantitative information may be compared for example, between centers that use different system scan parameters (e.g., saturation duration and relaxation delay) used to acquire the MR images.

Figure 10:
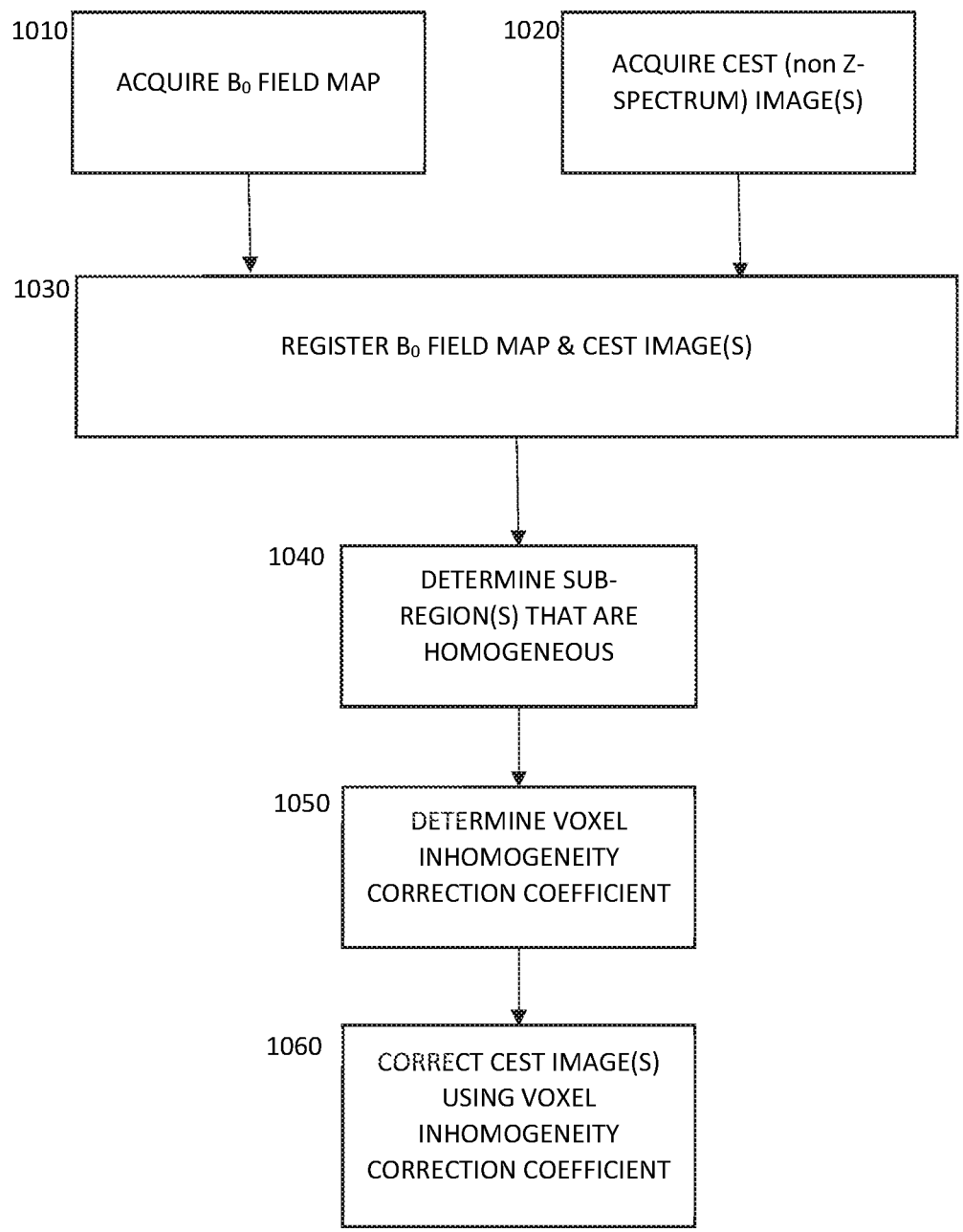
FIG. 10 shows an example 1000 of a field map-based voxel inhomogeneity correction method for CEST imaging without the need of Z-spectrum according to embodiments.

For example, the standardizing step 160 may be performed on CEST/MT Z-spectral images corrected according to embodiments, for example, a method 300 (see FIG. 3) and/or may be performed on CEST/MT (non Z-spectrum)

image(s) corrected according to embodiments, for example, according to a method 1000 (see FIG. 10). The standardizing step 160 may also be performed on CEST Z-spectral and/or CEST (non Z-spectrum) images and/or MT Z-spectral images and/or MT (non Z-spectrum) image(s) that have been corrected in steps 140 and 150 using other known or available methods.

In some embodiments, in the step 160, each voxel or a component of the corrected images/spectra for each offset may be standardized using a quasi-steady state CEST effect (e.g., the quasi-steady state signal ($I/I_0$)). In some embodiments, the quasi-steady state signal ($I/I_0$) for each voxel/component of the image/spectrum may be determined using a steady state spinlock relaxation rate ($R_{1\rho}$) calculated using a tilt angle ($\theta$) calculated from the corrected image/spectrum, scan parameters, parameters determined from the T1 map, B1 map, and scan parameters. FIGS. 13-16D show examples of determining the quasi-steady state CEST effect and one or more measurements according to embodiments.

Using this effect, the images may then be standardized so that the images/spectrum may be compared between different machines, scanning parameters, among others, or any combination thereof. For example, this can facilitate the use of CEST Z-spectral and/or CEST (non-spectrum) images in multi-center studies. This can offer flexibility to choose short saturation duration and relaxation delay experimentally when the scan time needs to be minimized, and the steady-state effect can be generated afterwards.

After the image(s) is corrected in step 150 and/or (optionally) standardized in step 160, the method 100 may include a step 170 of outputting the corrected and/or standardized, corrected and/or standardized images, associated quantitative information, among others, or any combination thereof.

In some embodiments, the step 170 may include determining or generating quantitative information. The quantitative information may include but is not limited to one or more measurements; one or more quantitative images (of the region of interest based on the corrected and/or standardized data (e.g., image(s)/spectrum), the one or more measurements, among others, or a combination thereof; other information; or any combination thereof. In some embodiments, the one or more measurements may include soft-tissue measurements, morphological studies, chemical-shift measurements, magnetization-transfer measurements, MRS, measurements of one or more types of nuclear Overhauser effect measurements, and/or functional imaging. By way of specific examples, the one or more measurements may include tissue pH, temperature, creatine level, phosphocreatine level, glycogen level, glucose level, total amide proton level, among others, or any combination thereof.

In some embodiments, the step 170 may include generating a report using the quantitative information, images, among others, or any combination thereof.

Figure 3:
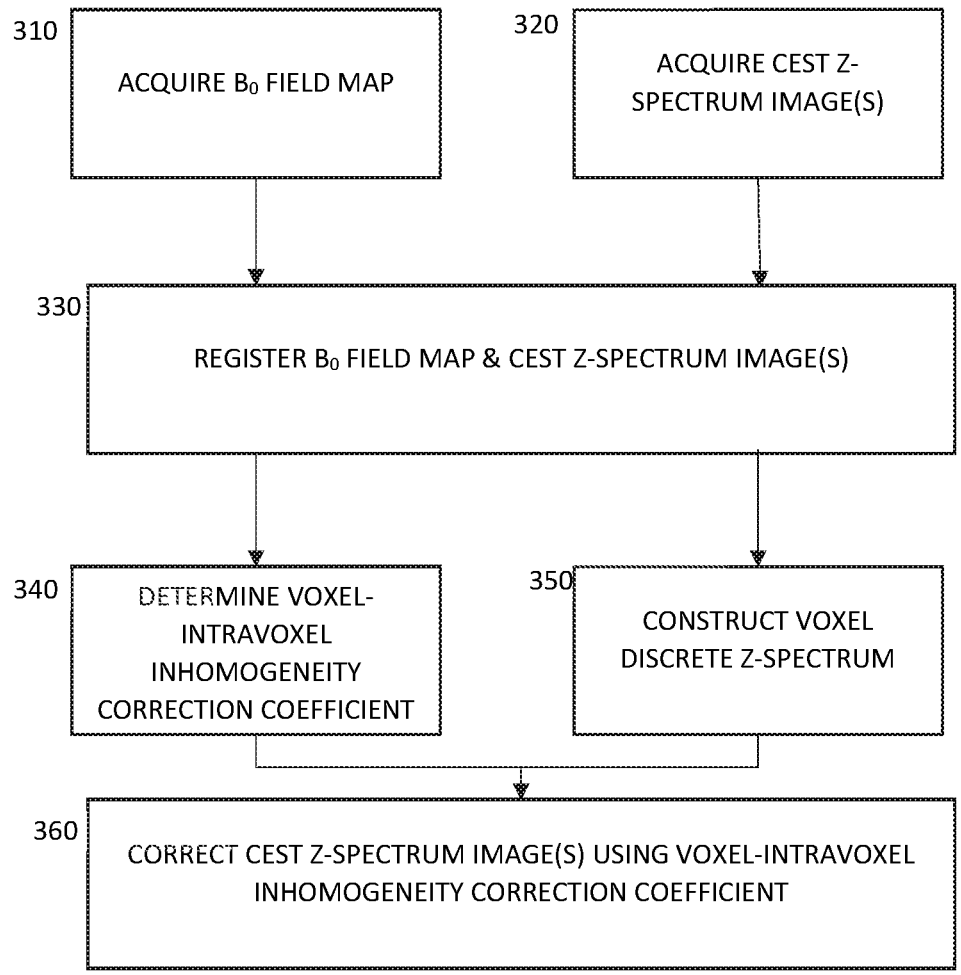
FIG. 3 shows an example of a high-resolution field map-based inhomogeneity correction method for CEST Z-spectral imaging according to embodiments.

FIG. 3 shows an example 300 of a high-resolution field map-based CEST intravoxel inhomogeneity correction (CIVIC) method for CEST Z-spectral imaging or MT Z-spectral imaging according to embodiments. As shown in FIG. 3, the method 300 may include a step 310 of acquiring a $B_0$ inhomogeneity field map and a step 320 of acquiring CEST/MT Z-spectrum image(s).

In some embodiments, the $B_0$ inhomogeneity field map may be a high resolution. The high resolution ("HR") $B_0$ inhomogeneity field map may be acquired or constructed using any available methods. For example, the $B_0$ inhomogeneity field map may be acquired using available methods. By way of example, the $B_0$ inhomogeneity field map can be constructed by interpolation of a Water saturation shift referencing ("WASSR") map, non-high resolution (or routine) $B_0$ inhomogeneity field map resolution field map, directly from an acquired high resolution $B_0$ inhomogeneity field map, among others, or a combination thereof. For example, $B_0$ inhomogeneity field map may be determined using the CEST Z-spectrum image(s). By way of example, the lowest point of the WASSR Z-spectrum can be determined either by symmetry analysis or fitting, which is taken as the bulk water resonance frequency, and the difference between the WASSR resonance frequency and that from the water resonance may be considered as the $B_0$ field inhomogeneity.

In some embodiments, the CEST/MT Z-spectrum image(s) may be acquired using any available methods. In some embodiments, the CEST/MT Z-spectrum image(s) may be non-high resolution CEST/MT MRI data.

In some embodiments, the method 300 may include a step 330 of registering the (reconstructed, high resolution) $B_0$ inhomogeneity field map to the CEST/MT Z-spectrum image(s) using any available methods.

The method 300 may further include a step 340 of determining an intravoxel inhomogeneity correction coefficient for each voxel using the constructed data. For example, the step 340 may include constructing a point-spread-function (PSF) from the HR subvoxel field inhomogeneity map, per voxel of CEST images for the region of interest.

By way of example, each voxel of CEST/MT image corresponds to multiple subvoxels of the high-resolution $B_0$ inhomogeneity map, for example, as shown in FIG. 2B. Such subvoxel information can be used to generate the $B_0$ point spread function (PSF). For example, the histogram (e.g. the frequency of $B_0$ inhomogeneity and whose width is equal to a given interval), may be determined based on the subvoxels $B_0$ for each voxel. Because the $B_0$ inhomogeneity PSF may have very different frequency characteristics from that of Z-spectrum, the histogram can be built using a reasonably given interval depending on the typical field inhomogeneity, for example, with intervals of 1 Hz. This subvoxel discrete $B_0$ field response for each voxel may be represented by the intravoxel inhomogeneity correction coefficient for that voxel. In some embodiments, the intravoxel inhomogeneity correction coefficient may also be determined using other available methods.

In some embodiments, the method 300 may include a step 350 of constructing voxel discrete Z-spectrum. In some embodiments, the step 350 may include constructing CEST spectrum/spectra from non-HR CEST images, per voxel of CEST images, or for each region of interest (ROI). In some embodiments, for the step 350, the CEST Z-spectrum can be constructed using the same interval of $B_0$ PSF (e.g., 1 Hz), per voxel.

In some embodiments, the method 300 may include a step 360 of correcting the CEST/MT Z-spectrum using the intravoxel inhomogeneity correction coefficient. For example, the step 360 may include deconvolving the intravoxel inhomogeneity correction coefficient (e.g., subvoxel field inhomogeneity PSF) from the CEST/MT Z-spectral images, per voxel/ROI.

In some embodiments, after the construction of $B_0$ PSF and Z-spectrum, the $B_0$ PSF can be deconvolved from the Z-spectrum. For example, $Z_{app} Z_{orig} \odot \Delta B_0$, where $Z_{app}$ is the apparent Z spectrum obtained with $B_0$ heterogeneity, and $Z_{orig}$ is the desired Z spectrum in the absence of $B_0$ heterogeneity, in which $\Delta B_0$ is subvoxel magnetic field function. The step 360 is not limited to the deconvolution method described and may use additional and/or alternative methods, such as numerical fitting.

In some embodiments, the method 300 may also include a step 370 of resampling the CEST/MT Z-spectrum/images using the intravoxel inhomogeneity correction coefficient for each voxel of the region of interest (i.e., the deconvolution-reconstructed signal for CEST Z-spectrum/images, per voxel/ROI). By way of example, the restored $Z_{orig}$ has the same interval as the intravoxel $B_0$ inhomogeneity PSF, which can be resampled to any given interval, for example, the original Z-spectral frequency interval.

FIGS. 4A-D shows an example of the application of the CIVIC method according to embodiments. FIG. 4A shows an example of a simulated Z-spectrum without $B_0$ inhomogeneity. FIG. 4B shows an example of a simulated symmetric $B_0$ inhomogeneity dispersion within a single CEST MM voxel or ROI. FIG. 4C shows the apparent Z-spectrum in the presence of symmetric $B_0$ inhomogeneity dispersion. As shown in this figure, the routine interpolation and shift-based $B_0$ inhomogeneity correction approach fails to correct symmetric $B_0$ inhomogeneity dispersion. FIG. 4D shows that using the method shown in FIG. 3, the original Z spectrum has been recovered and is in agreement with FIG. 4A.

FIGS. 5A-F shows another example of the application of the CIVIC method according to embodiments. FIG. 5A shows an example of a $B_0$ field inhomogeneity map determined from water saturation shift referencing (WASSR) approach. FIG. 5B shows an example of a high-resolution $B_0$ field inhomogeneity map. FIG. 5C shows that the per-pixel $B_0$ field inhomogeneity (FIG. 5A) and averaged subvoxel $B_0$ field inhomogeneity (FIG. 5B) per voxel are highly correlated in this example. FIGS. 5D and 5E show CEST images ($MTR_{asym}$) obtained from conventional interpolation correction and the CIVIC correction, respectively. FIG. 5F shows the correlation of the corrections. As shown in this figure, both corrections are highly correlated.

FIGS. 6A-C illustrate another example of the application of the CIVIC method according to embodiments. FIG. 6A shows an example of a Z spectrum from a single voxel. FIG. 6B shows the subvoxel $B_0$ field inhomogeneity for the pixel shown in FIG. 6A. In this example, there are 10 subvoxels for each voxel. FIG. 6C shows the reconstructed Z-spectrum after correction using the subvoxel inhomogeneity correction coefficient according to the method 300. As shown in FIG. 6C, the CIVIC correction resets the center of Z-spectrum to 0 ppm. In addition, the signal intensity at 0 ppm (FIG. 6C) is much closer to 0 than the raw CEST Z-spectrum (FIG. 6A). These markers show improved subvoxel inhomogeneity correction.

Figure 7:
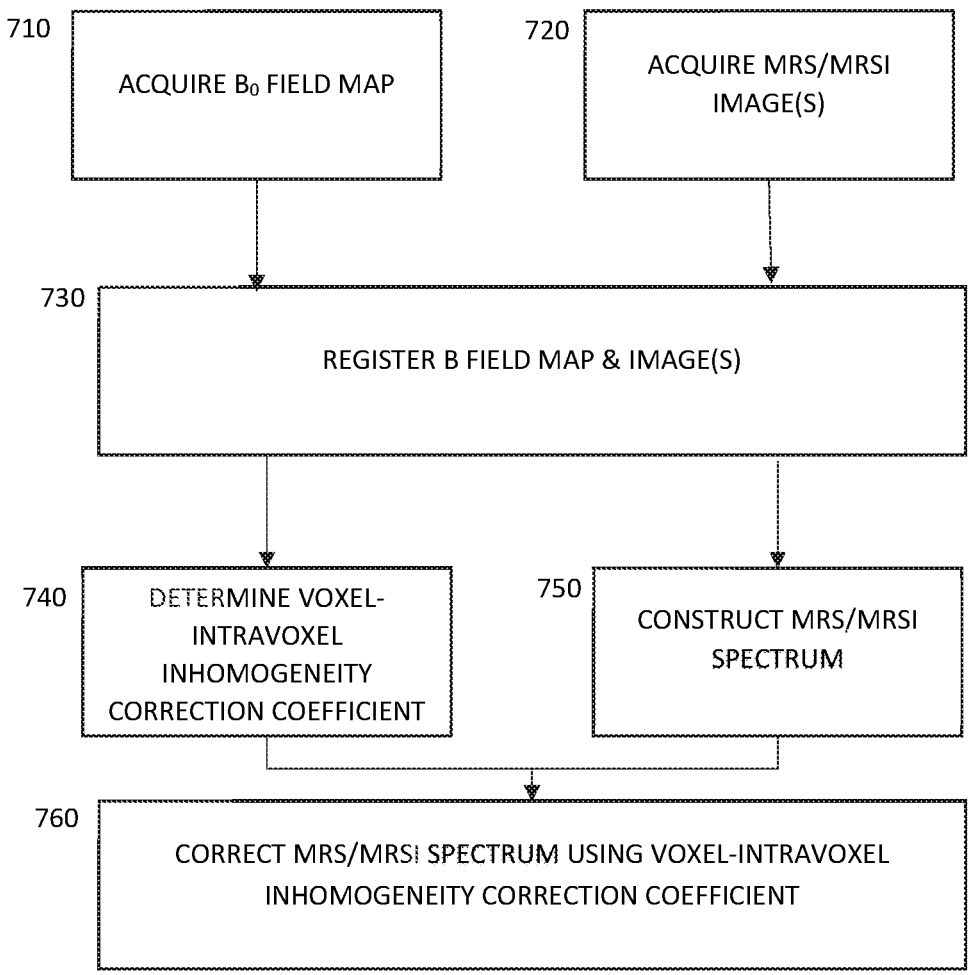
FIG. 7 shows an example of an application of the high-resolution field map-based inhomogeneity correction method for MRS/MRSI image(s)/spectrum.

FIG. 7 shows an example 700 of a high-resolution field map-based inhomogeneity correction (CIVIC) method for single-voxel MRS or MRS imaging (MRSI) according to embodiments.

As shown in FIG. 7, the method 700 may include a step 710 of acquiring a $B_0$ inhomogeneity field map and a step 720 of acquiring MRS/MRSI using any available methods. In some embodiments, the $B_0$ inhomogeneity field map may be a high resolution. The high resolution ("HR") $B_0$ inhomogeneity field map may be acquired or constructed using any available methods. For example, the $B_0$ inhomogeneity field map is acquired using available methods.

By way of example, step 710 may include acquiring field inhomogeneity map and step 720 may include acquiring MRS/MRSI.

In some embodiments, the method 700 may include a step 730 of registering the (reconstructed, high resolution) $B_0$ inhomogeneity field map to the MRS/MRSI using available methods.

The method 700 may further include a step 740 of determining the intravoxel inhomogeneity correction coefficient and a step 750 of constructing the MRS/MRSI spectrum using available methods. For example, the step 740 may include constructing a point-spread-function (PSF) from the HR subvoxel field inhomogeneity map, per voxel of MRS/MRSI spectrum for the region of interest.

Next, the method 700 may include a step 760 of correcting the MRS/MRSI spectrum using the intravoxel inhomogeneity correction coefficient. By way of example, the step 760 may be performed on real and/or imaginary signals of the MR spectrum (MRS). In some embodiments, the step 760 may depend on the complex signal of the MR spectrum with automated and/or manual phase adjustment. In some embodiments, the step 760 may include deconvolving the $B_0$ PSF from the constructed spectrum. For example, the deconvolving the subvoxel field inhomogeneity PSF may be for MRS, per voxel/ROI of MRSI.

For example, the correcting (step 760) can be performed on a phased spectrum, performed on real and imaginary signals independently, among others, or a combination thereof. After the MRS signal (real, imaginary, complex and/or phase-corrected magnitude) is corrected, the signal may be reconstructed to correct for field inhomogeneity.

By way of example, the processing can be performed on the MRS magnitude spectrum after phase adjustment. In this example, $MRS_{app}=MRS_{orig} \odot PSF$, where $MRS_{app}$ and $MRS_{orig}$ are the apparent MRS signal with $B_0$ heterogeneity and "genuine" MRS signal without $B_0$ heterogeneity, respectively, in which PSF is subvoxel field inhomogeneity function.

Figure 8A:
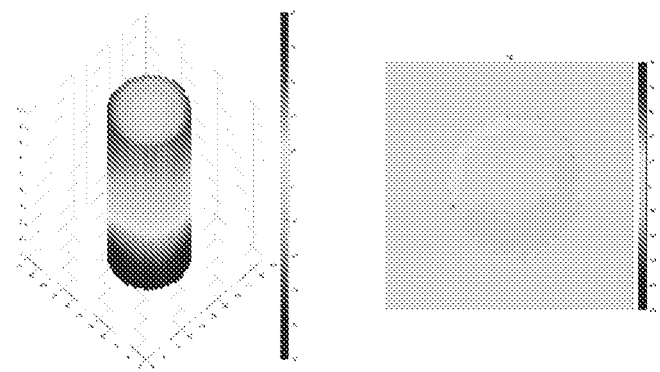
FIGS. 8A and 8B show examples of a field map under good field homogeneity (with high-order shimming) and another field map under poor field homogeneity (without high-order shimming), respectively.
Figure 8B:
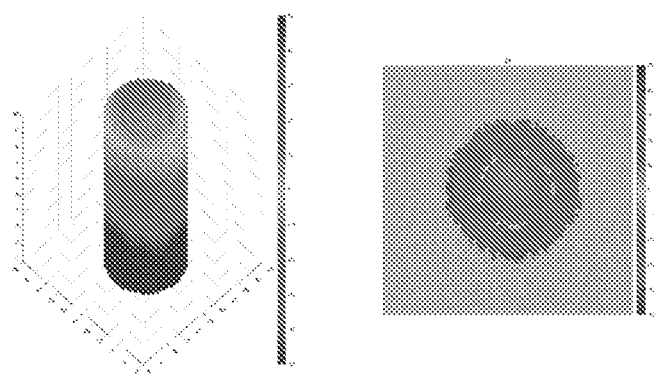

FIGS. 8A and 8B and FIGS. 9A-C show examples of the application of high-resolution field map-based inhomogeneity correction (CIVIC) method for single-voxel MRS according to embodiments. FIG. 8A shows the high-resolution field map with higher-order gradient shimming condition and FIG. 8B shows high-resolution field map without higher-order gradient shimming condition. A single voxel MRS was acquired from a voxel of 1 cm×1 cm×1 cm under these two shimming conditions.

Figures 9A, 9B, 9C:
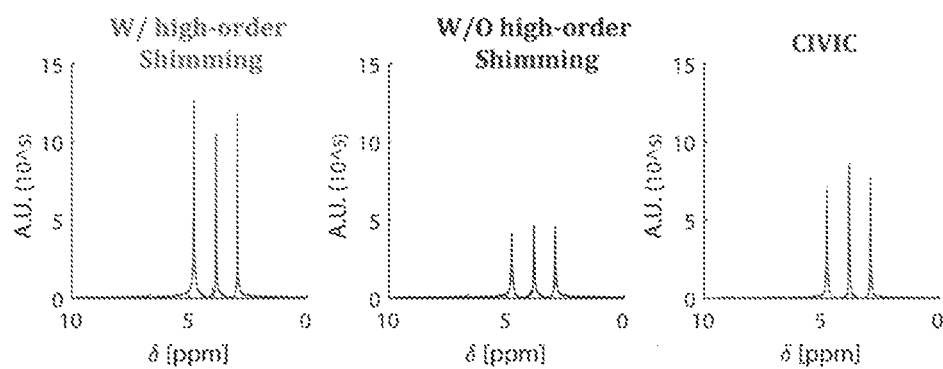
FIGS. 9A and 9B show MRS spectra obtained from FIGS. 8A and 8B, respectively.
FIG. 9C shows intravoxel field inhomogeneity corrected MRS spectrum (FIG. 9B).

FIGS. 9A-C show the effectiveness of CIVIC in improving MRS measurements from a creatine-gel phantom. FIG. 9A shows MRS that acquired under high-order gradient shimming condition (FIG. 8A) and FIG. 9B shows the single-voxel MRS that was acquired without high order gradient shimming condition (FIG. 8B). In this example, the 3D high-resolution field maps were obtained from a field of view of 5 cm×5 cm×9.6 cm with a matrix size of 64×64×96. The high-resolution field maps have a spatial resolution of 0.78 mm×0.78 mm×1 mm. The single MRS voxel (1 cm×1 cm×1 cm) corresponds to 13×13×10 subvoxels (i.e., 1690) of high-resolution field map. FIG. 9C shows the MRS after correction using the subvoxel inhomogeneity correction coefficient according to the method 700. As shown, FIG. 9C has a higher signal intensity and narrower spectral width than that of FIG. 9B, closer to the MRS spectrum obtained under the good shimming condition (FIG. 9A).

FIG. 10 shows an example of a method 1000 of a field map-based voxel inhomogeneity correction method for CEST imaging or MT imaging without the need of Z-spectrum according to embodiments. By not requiring Z-spectral scans, this example can result in a substantial reduction in scan time, which can be critical for the emergency setting such as acute stroke imaging. In this example, the regression between the apparent CEST effect and $B_0$ inhomogeneity can be used to establish the CEST-$B_0$ response spectrum, from which, field inhomogeneity can be corrected without Z-spectral scans. In some embodiments, the method 1000 may be performed with and/or without a method to correct for intravoxel inhomogeneity, such as the method 300 described in FIG. 3. By way of example, the output of the method 1000 may be used as an input (step 320) for the method 300. In another example, the method 1000 may be performed without the method 300.

As shown in FIG. 10, the method 1000 may include a step 1010 of acquiring a $B_0$ inhomogeneity field map and a step 1020 of acquiring CEST/MT (non Z-spectrum) image(s)/spectrum. In some embodiments, the $B_0$ inhomogeneity field map may be high resolution. The high resolution ("HR") $B_0$ inhomogeneity field map may be acquired or constructed using any available methods.

For example, the $B_0$ inhomogeneity field map may be acquired using available methods. By way of example, the $B_0$ inhomogeneity field map can be constructed by interpolation of a Water saturation shift referencing ("WASSR") map, non-high resolution (or routine) $B_0$ inhomogeneity field map resolution field map, directly from an acquired high resolution $B_0$ inhomogeneity field map, among others, or a combination thereof. For example, the $B_0$ inhomogeneity field map may be determined using the CEST/MT Z-spectrum image(s). By way of example, the lowest point of the WAS SR Z-spectrum can be determined either by symmetry analysis or fitting, which is taken as the bulk water resonance frequency, and the difference between the WAS SR resonance frequency and that from the water resonance may be considered as the $B_0$ field inhomogeneity.

In some embodiments, the CEST/MT (non Z-spectrum) image(s)/spectrum may be acquired using available methods. For example, the CEST/MT images (in the absence of Z spectrum) may be acquired by calculating CEST map using $$CESTR = \frac{I_{ref} - I_{label}}{I_0},$$

where $I_0$ is the control image without RF irradiation and $I_{ref,label}$ are the label and reference images with RF irradiation applied at label and reference frequency offsets, respectively. In other embodiments, other methods may be used. By way of example, it can be other means of CEST effect quantification, such as CEST-specific magnetization transfer and relaxation normalized APT (MRAPT) image (Guo et al. Neuroimage 2016; 141:242-9; Wang et al. Neuroimage 2019; 191:610-7).

In some embodiments, the method 1000 may include a step 1030 of registering the (reconstructed, high resolution) $B_0$ inhomogeneity field map to the non Z-spectrum CEST/MT image(s)/spectrum using any available methods.

The method 1000 may further include a step 1040 of determining one or more subregions that should have a uniform MRI effect (also referred to as "reference region(s)") of the region of interest. For example, one or more subregions may include a region of known normal tissue, such as intact brain white matter, gray matter, and/or a combination thereof.

The method 1000 may include a step 1050 of determining the field inhomogeneity correction coefficient for each voxel of the one or more reference regions or subregions. The voxel-wise inhomogeneity correction coefficient may be determined using linear regression. By way of example, the correction coefficient may be determined in simple phantoms where there is one exchange group with water (2-pool) model. In another example, for example, pH imaging, white matter (WM)/gray matter (GM) heterogeneity may be determined because they have little pH difference (see for example, Guo et al. Neuroimage 2016; 141:242-9; Wang et al. Neuroimage 2019; 191:610-7). By modeling the $B_0$ inhomogeneity effect using a regression function, their effect can be accounted for and be used to restore the original CEST effect using $CESTR_{app} \approx CESTR_{orig} + [C_1 \cdot \Delta\omega_s + C_2 \cdot \Delta\omega_s^2]$ or numerical fitting $CESTR_{app} \approx CESTR_{orig} + F[\Delta\omega_s, \Delta\omega_s^2]$. In other embodiments, the voxel field inhomogeneity correction coefficient may be determined using other methods/function than this linear regression.

By establishing the voxel-wise dependence of $B_0$ and CEST/MT MRI signal, it can be treated as a segment of the spectrum, which the CIVIC correction applies.

In some embodiments, the method 1000 may include a step 1060 of correcting the other (sub)regions of the region of interest and/or the entire region of interest (e.g., brain) of the $B_0$ map (step 1010) and CEST map (step 1020) using this coefficient.

FIGS. 11A-F and 12A-H show examples of the application of the regression $B_0$ correction method using non-Z spectrum CEST (MRAPTR) images according to embodiments. FIGS. 11A-F shows an application of fast $B_0$ inhomogeneity correction without Z-spectrum in a dual pH phantom. FIG. 11A shows a raw MTR asymmetry ($MTR_{asym}$) image calculated from an asymmetry analysis, with noticeable $B_0$ inhomogeneity artifact. FIG. 11B shows the $B_0$ inhomogeneity map determined from the WASSR scan. FIG. 11C shows a regression analysis between $B_0$ inhomogeneity and raw $MTR_{asym}$, per pixel for each ROI (interior and exterior compartment). FIG. 11D shows fast $B_0$ inhomogeneity-corrected $MTR_{asym}$(fast) map. FIG. 11E shows interpolation-based $B_0$ inhomogeneity-corrected $MTR_{asym}$ (intrpl) map. FIG. 11F shows regression analysis between $MTR_{asym}$ (fast) and $MTR_{asym}$ (intrpl), per pixel.

FIGS. 12A-H show an example of in vivo fast $B_0$ inhomogeneity correction in a representative normal adult rat brain regression $B_0$ correction method according to embodiments. FIG. 12A shows an example of an acquired mean magnetization transfer ratio (MMTR) at ±3.5 ppm. FIG. 12B shows an example of an acquired pH-sensitive $MTR_{asym}$ map. FIG. 12C shows pH-specific $\Delta$MRAPTR map without $B_0$ inhomogeneity correction. FIG. 12D shows a pH map determined from $\Delta$MRAPTR map without $B_0$ inhomogeneity correction. $B_0$ inhomogeneity map determined from the WASSR scan is shown in FIG. 12E. The regression analysis between $B_0$ inhomogeneity and raw $\Delta$MRAPTR, per pixel, is shown in FIG. 12F. FIG. 12G shows $\Delta$MRAPTR map with the proposed fast $B_0$ inhomogeneity correction, with the corresponding pH map shown in FIG. 12H.

Figure 13:
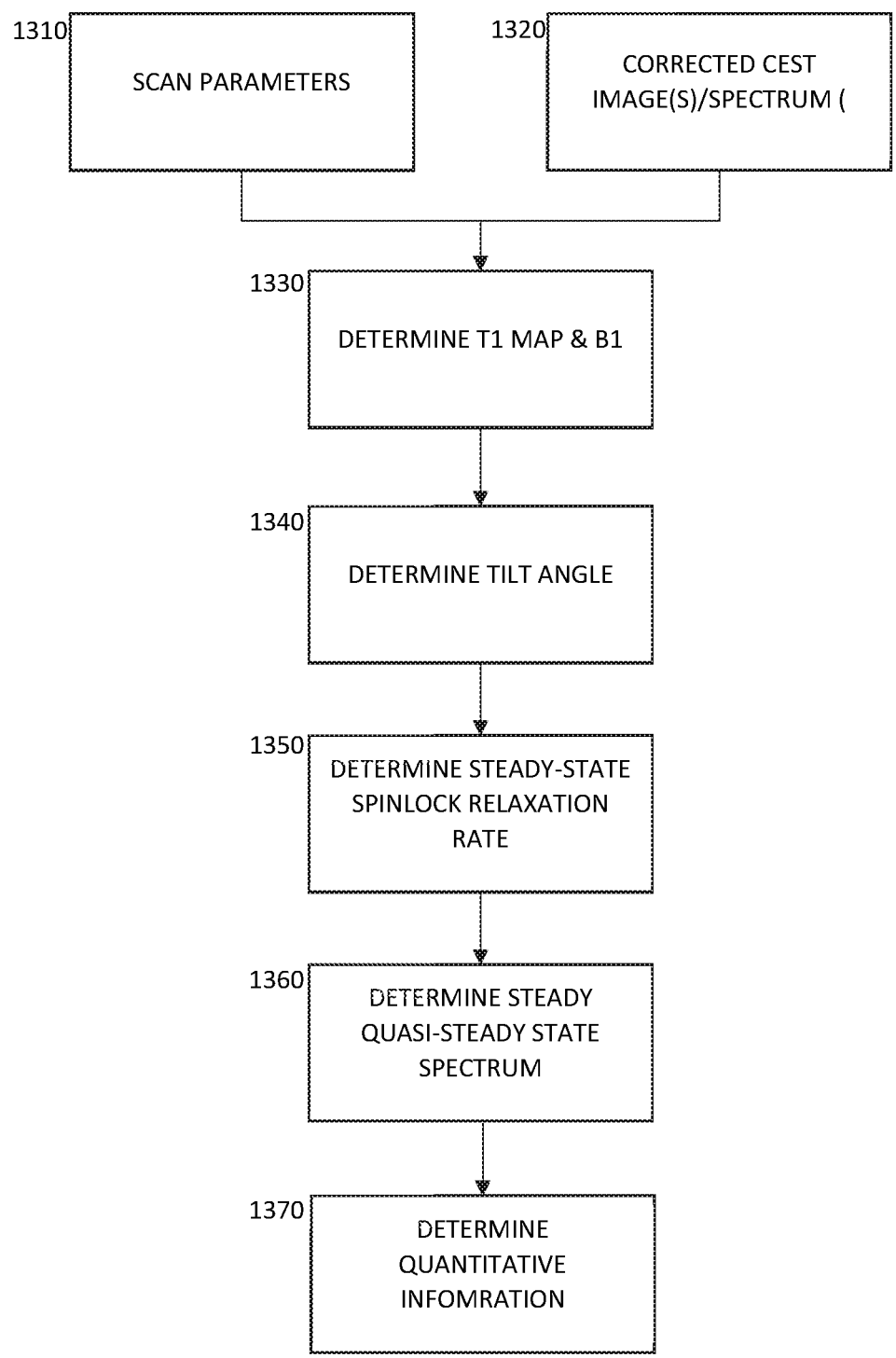
FIG. 13 shows an example 1300 of a standardization method for corrected CEST/MT MR image(s)/spectrum according to embodiments.

FIG. 13 shows an example 1300 of a standardization method for corrected MR images/spectrum (e.g., CEST/MT Z-spectral, CEST/MT (non Z-spectrum) image(s) and/or CEST MRS/MRSI)), for example, from step 150, according to embodiments. In some embodiments, the corrected MR images/spectrum may correspond to corrected CEST/MT Z-spectral images, for example, using the method 300 (see FIG. 3) and/or corrected CEST/MT (non Z-spectrum) image(s) according to embodiments, for example, using the method 1000 (see FIG. 10). In some embodiments, the inhomogeneity for CEST/MT Z-spectral, CEST/MT (non Z-spectrum) image(s) and/or CEST MRS/MRSI may be corrected using other methods. In some embodiments, the standardization method may be applied per voxel for each saturation offset.

The standardization method can improve sensitivity without needing a long-scan time. The standardization can derive the quasi-steady-state even when the experimental saturation duration and relaxation delay are generally not long. This can enable a reduction of the scan time without the loss of the magnitude of the CEST contrast.

In some embodiments, the step 1300 may include a step 1310 of acquiring the scan parameters, such as saturation duration and relaxation delay, associated with the corrected MR images/spectrum (step 1320), for example, from step 150 (e.g., corrected CEST/MT images/spectrum).

In some embodiments, the method 1300 may include a step 1330 of determining T1 map and B1 using the corrected MR images/spectrum and/or scan parameters. In some embodiments, the T1 map and B1 may be determined using known methods. For example, the T1 map may be determined using inversion recovery methods, saturation recovery methods, look-locker methods, MR fingerprint (MRF) techniques methods, among others, or any combination thereof. For example, B1 may correspond to the amplitude of RF saturation when B1 field is homogenous, may be determined from a B1 map (e.g., determined from known methods such as double angle method (DAM) if B1 field is not homogenous, may be determined using other methods, or any combination thereof.

For example, if standardization is applied per voxel with CEST scan (one offset a time), the corresponding T1 and B1 values may be either direct measurement of the voxel(s). If standardization is applied to CEST MRS/MRSI, corresponding T1 and B1 values may be either direct measurement of the voxel(s) or co-registered from images (MRS voxel is often larger than image voxel).

In some embodiments, the method 1300 may further include a step 1340 of determining the tilt angle (θ) for each pixel/voxel. In some embodiments, the title angle (θ) may be determined using the gyromagnetic ratio (γ), amplitude of RF saturation pulse ($B_1$), and offset of the RF saturation pulse (Δω). For example, the title angle (θ) may be determined using the following:

$$\theta = a\tan\left(\frac{\gamma B_1}{\Delta\omega}\right). \quad (1)$$

After which, the method 1300 may include a step 1350 of determining a steady state spinlock relaxation rate ($R_{1\rho}$) using the calculated tilt angle (θ). Because the inhomogeneity has been corrected in spectrum/image(s), the calculated tilt angle (θ) may be effectively used to calculate a steady state spinlock relaxation rate ($R_{1\rho}$).

In some embodiments, the steady state spinlock relaxation rate ($R_{1\rho}$) for each pixel or voxel may be determined using the calculated tilt angle (θ), scan parameters, parameters determined from the T1 map, B1 map, among others, or any combination thereof.

For example, the steady state spinlock relaxation rate ($R_{1\rho}$) may be determined using the following:

$$\frac{I_{sat}^{app}}{I_0^{app}} \cdot \left\{\frac{1 - e^{-R_{1w} \cdot (Ts+Td)}}{1 - e^{-R_{1w} \cdot Td}}\right\} = e^{-R_{1\rho} \cdot Ts} + \left\{\frac{R_{1w}}{R_{1\rho} \cdot (1 - e^{-R_{1w} \cdot Td})}\cos^2\theta\right\} \cdot (1 - e^{-R_{1\rho} \cdot Ts}). \quad (2)$$

In equation (2), $I_{sat}^{app}$ corresponds to saturated scan acquired from the CEST image/spectrum, $I_0^{app}$ corresponds to unsaturated control scan acquired from the CEST image/spectrum, Ts corresponds to saturation time provided in the scan parameters, Td corresponds to relaxation delay provided in the scan parameters, θ corresponds to the calculated tilt angle, and $R_{1w}$ corresponds to the bulk water transverse relaxation rate acquired from the T1 map from the step 1330 (e.g., $T_{1w}$ map (i.e., $R_{1w}=1/T_{1w}$)). In some embodiments, $R_{1w}$ and/or $R_{1\rho}$ from Eq. 2 may be determined using other methods/techniques, such as numerical solution, modified MR fingerprinting (MRF) and/or machine learning.

In some embodiments, the method 1300 may include a step 1360 of determining a quasi-steady state signal ($I/I_0$) for each voxel or component for each saturation offset using the calculated tilt angle (θ), the calculated spinlock relaxation rate ($R_{1\rho}$), and the calculated bulk water transverse relaxation rate ($R_{1w}$). For example, the quasi-steady state signal ($I/I_0$) may be determined using the following:

$$I/I_0 = (R_{1w}/R_{1\rho})\cos^2\theta \quad (3).$$

In some embodiments, the method 1300 may include a step 1370 of generating/determining quantitative information. In some embodiments, the quantitative information may include one or more measurements determined based on the standardized voxel/component (the quasi-steady state signal ($I/I_0$) from step 1360) for each saturation offset; one or more quantitative images using the one or more measurements, the standardized voxel/component; among others; or any combination thereof. In some embodiments, the one or more measurements may include but is not limited to CEST asymmetry (CESTR) image, the CEST exchange effect ($R_{ex}$), labile proton concentration, labile proton exchange rate, among others, or any combination thereof. For example, the CESTR may be determined using the following:

$$CESTR = \frac{I_{ref}}{I_0} - \frac{I_{label}}{I_0}, \text{where } \frac{I_{ref}}{I_0} \text{ and } \frac{I_{label}}{I_0}$$

are the quasi-steady-state CEST signals at the reference and label frequency offsets, respectively.

For example, the CEST exchange effect ($R_{ex}$) may be determined using (standardized) spinlock relaxation rate ($R_{1\rho}$) (determined using the standardized image and the tilt angle (θ). For example, the ($R_{ex}$) may be determined using the following:

$$R_{ex} = R_{1\rho} - R_{1w}\cos^2\theta - R_{2w}\sin^2\theta \quad (4).$$

Figures 14A, 14B:
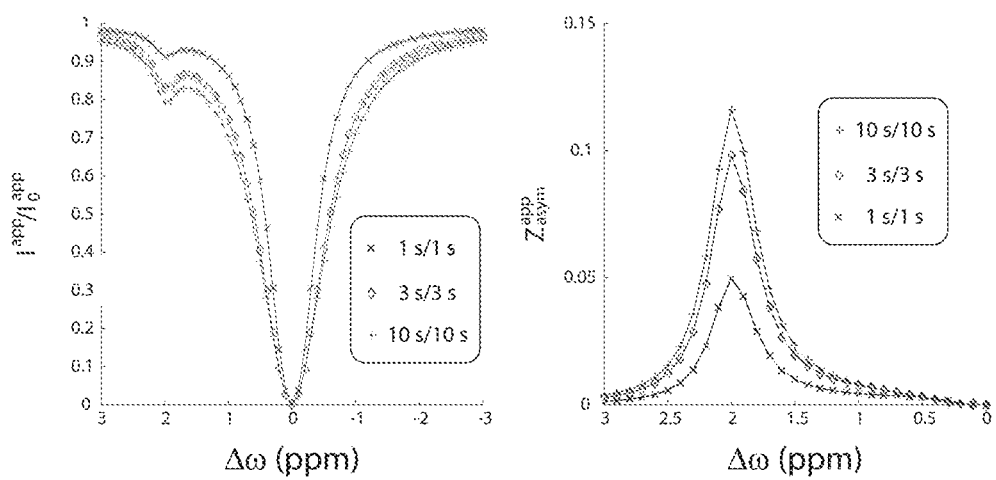
FIGS. 14A-C show an example of a simulation of the dependence of CEST MRI on saturation time and relaxation delay.
Figure 14C:
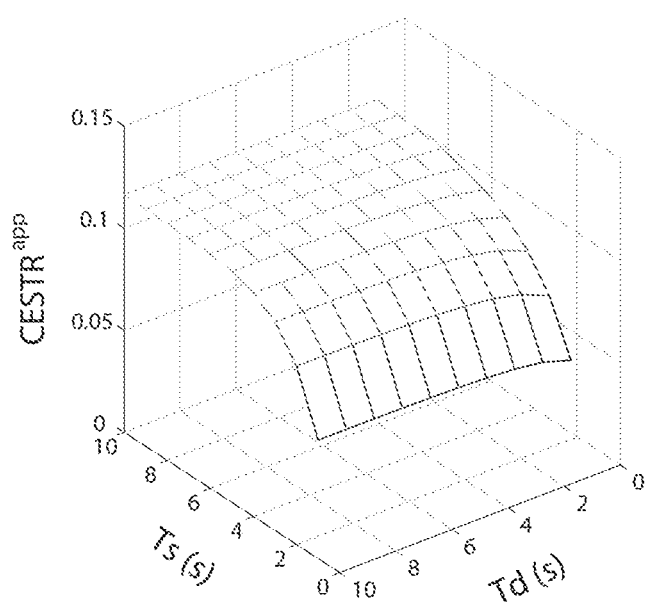

FIGS. 14A-C shows an example of a simulation of the effect of Td and Ts on the CEST MM effect. FIG. 14A shows three representative Z-spectra under short Td and Ts (i.e., Td=1 s/Ts=1 s, x markers), moderate Td, and Ts (i.e., 3 s/3 s, diamond markers), and long Td and Ts (i.e., 10 s/ 10 s, + markers). For the simulation, we assumed $T_{1w}$=2 s. As shown in FIG. 14A, the Z-spectral intensity drops at a long saturation duration and relaxation delay, as expected. FIG. 14B plots the corresponding Z-spectra asymmetry under the three representative Td and Ts, which increases with the saturation duration and relaxation delay. FIG. 14C shows the CEST effect as a function of saturation time and relaxation delay, indicating dependence on the saturation time and relaxation delay, as expected. Such a strong dependence of CESTR over Td and Ts suggests the need to account for such experimental choice of saturation duration and relaxation delay when comparing results obtained under different experimental conditions. For the Z-spectrum simulation, it was assumed a typical labile proton ratio and an exchange rate of 1:1000 and 100 s⁻¹, respectively, with a labile proton chemical shift at 2 ppm for a magnetic field strength of 7 Tesla with RF saturation amplitude of 1 µT. The minimal and maximal CEST effect was 4.97% and 11.62%, respectively, with its mean and standard deviation being 10.34±1.86% and a coefficient of variance (COV) of 17.97%.

Figure 15A:
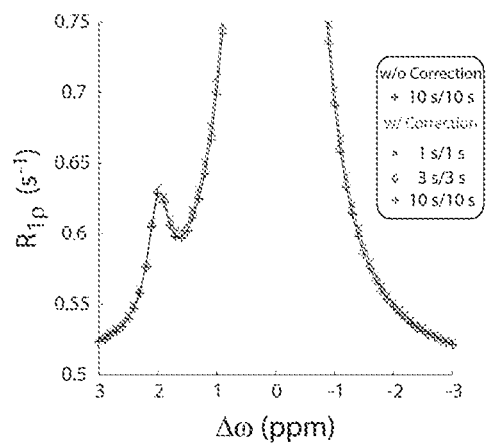
FIGS. 15A-D show an example of a simulation of a quasi-steady state CEST MM using the standardization method according to embodiments.
Figure 15B:
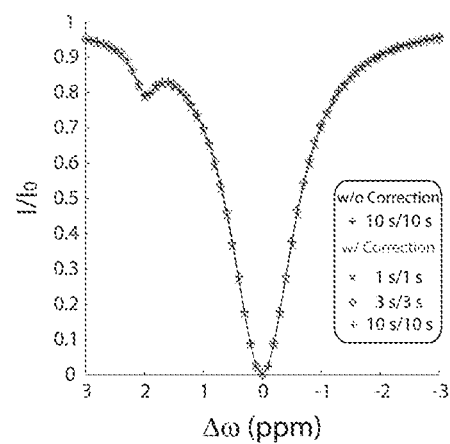
Figure 15C:
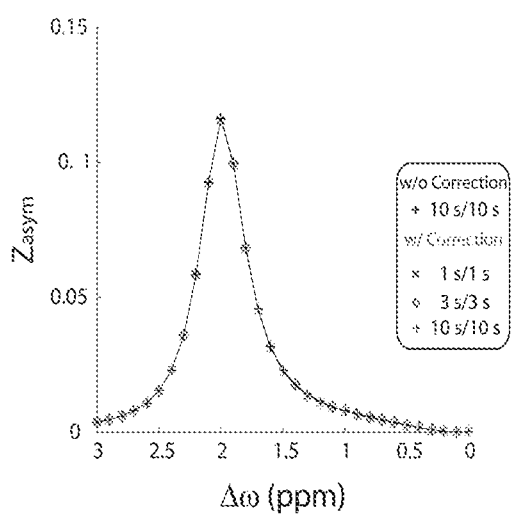
Figure 15D:
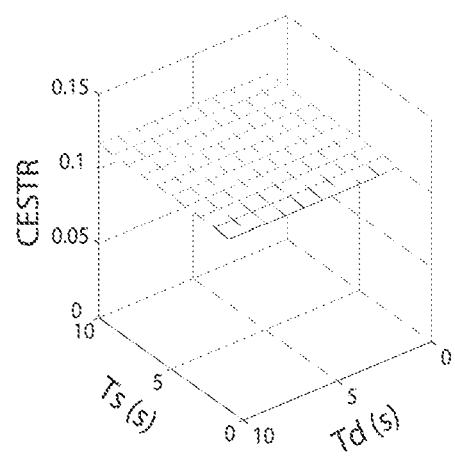

FIGS. 15A-C show an example of a simulation of the quasi-steady-state CEST MM using the steady-state method (FIG. 13) according to embodiments. FIG. 15A plots the quasi-steady-state $R_{1\rho}$ solved from three representative saturation time and relaxation delay, being 1 s/1 s (black cross markers), 3 s/3 s (black diamond markers), and 10 s/10 s (gray plus markers). As shown, the quasi-steady state $R_{1\rho}$ nearly overlapped with the apparent $R_{1\rho}$ $$\left(\text{i.e., } \frac{I_0^{app}}{I_{sat}^{app}} \cdot R_{1w}\cos^2\theta\right)$$

under the condition of long saturation time and relaxation delay (10 s/10 s, black plus markers). FIGS. 15B and 15C show reconstructed quasi-steady-state Z-spectra and asymmetry Z-spectra (e.g., 1 s/1 s (cross markers), 3 s/3 s (diamond markers), and 10 s/10 s gray plus markers)) and those obtained under long saturation time and relaxation delay (10 s/10 s (black plus markers)). FIG. 15D shows the CEST effect as a function of saturation time and relaxation delay. As shown, there is little variation between CEST effect. The minimal and maximal CEST effect was 11.44% and 11.64%, respectively, with its mean and standard deviation being 11.60±0.05% and a coefficient of variance of 0.42%. As shown, the quasi-steady-state CEST Mill effect can be in excellent agreement with the CEST effect at the long saturation time and relaxation delay (i.e., 11.62%). The coefficient of variation (COV) of the quasi-steady-state solution (FIG. 15D) is only 2.34% of that without correction (FIG. 14C), showing that the quasi-steady-state CEST MM effect determined using the standardization method (FIG. 13) according to embodiments can be effective in minimizing the effect of limited saturation duration and relaxation delay.

Figure 16A:
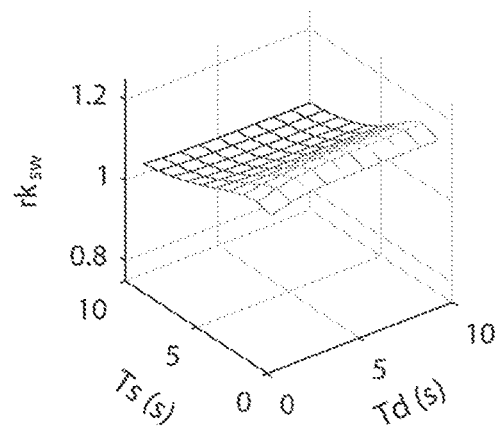
FIGS. 16A-D shows an example of a comparison of the numerally solved labile proton exchange rate and concentration as functions of the saturation duration and relaxation delay determined using the standardization method according to embodiments.
Figure 16B:
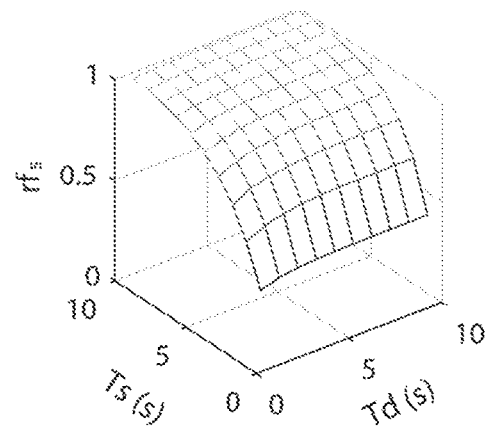
Figure 16C:
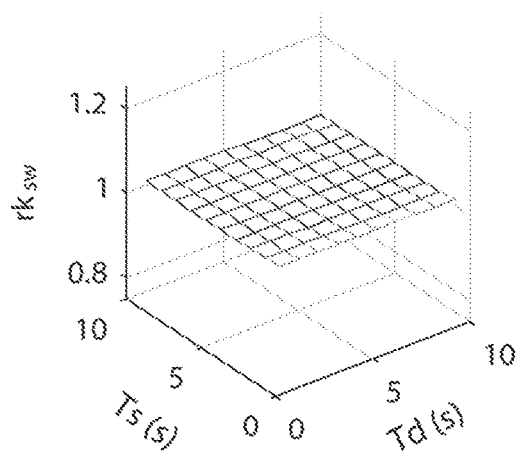
Figure 16D:
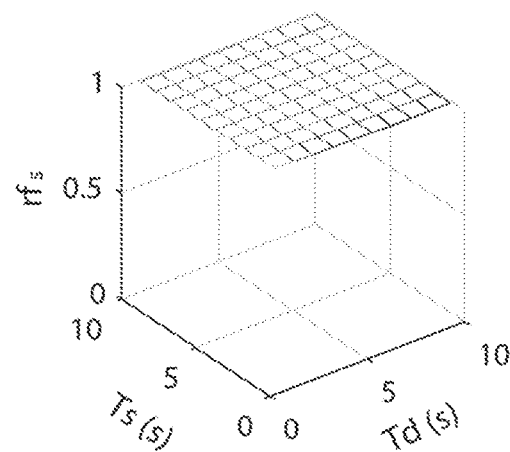

FIGS. 16A-D shows an example of a comparison of a numerically solved labile proton exchange rate and concentration as functions of the saturation duration and relaxation delay and determined using the steady-state method (FIG. 13) according to embodiments. FIG. 16A shows the normalized exchange rate determined from the omega plot of the apparent CEST effect as a function of Td and Ts. As shown, the relative labile proton exchange rate ($rk_{sw}$) was determined from the apparent CEST effect. The exchange rate can be overestimated when Ts is not sufficiently long, while the dependence on Td is less prominent than the Ts dependence. Correspondingly, FIG. 16B shows the normalized labile proton concentration determined from the omega plot of the apparent CEST effect, as a function of Td and Ts. As shown, the relative labile proton ratio ($rf_s$) was determined from the apparent CEST effect. It can be underestimated when Ts is not sufficiently long. In comparison, FIGS. 16C and 16D show the normalized labile proton exchange rate and ratio from the proposed quasi-steady-state solution. In FIG. 16C, the relative labile proton exchange rate ($rk_{sw}$) was determined from the quasi-steady-state CEST effect using the standardization method (FIG. 13) according to embodiments. In FIG. 16D, the relative labile proton ratio ($rf_s$) was determined from the quasi-steady-state CEST effect using the standardization method (FIG. 13) according to embodiments. As shown in FIGS. 16C and 16D, there can little dependence on Ts and Td and therefore the standardization method (FIG. 13) according to embodiments can reasonably account for the effect of limited saturation duration and recovery delay, permitting accurate quantification of the underlying CEST systems.

Figure 17:
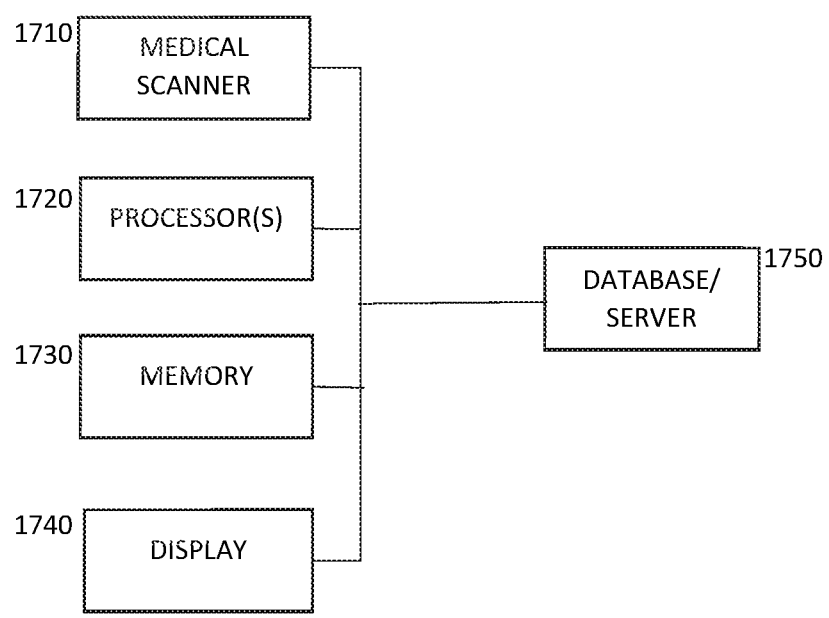
FIG. 17 shows a block diagram illustrating an example of a system according to embodiments.

FIG. 17 shows an example of a system 1700 for the determination of the correction coefficient. The system for carrying out the embodiments of the methods disclosed herein is not limited to the system shown in FIG. 17. Other systems may also be used. It is also to be understood that the system 1700 may omit any of the modules illustrated and/or may include additional modules not shown. By way of example, the system 1700 may include the server 1750 and a computer system (e.g., processor 1720, memory 1730, and display 1740) or the medical scanner with the computer system. In another example, the system is a computer or workstation instead of the medical scanner 1710, instead of the server 1750, or instead of both. In another example, the processor 1720, memory 1730, and display 1740 may be part of the medical scanner 1710. In further example, the processor 1720, memory 1730, and display 1740 may be a part of an archival and/or image processing system, such as associated with a medical records database workstation or server, separate from the medical scanner 1710. In other examples, the processor 1720, memory 1730, and display 1740 may be a personal computer, such as a desktop or laptop, a workstation, or combinations thereof. The image processor 1710, display 1740, and memory 1730 may be provided without other components for acquiring data by scanning a patient.

The system 1700 shown in FIG. 17 may include any number of modules that communicate with each other through electrical or data connections (not shown). In some embodiments, the modules may be connected via any network (e.g., wired network, wireless network, or any combination thereof).

In some embodiments, the system may include one or more processors 1720. The processor(s) 1720 may include one or more processing units, which may be any known processor or a microprocessor. For example, the processor(s) may include any known central processing unit (CPU), imaging processing unit, graphical processing unit (GPU) (e.g., capable of efficient arithmetic on large matrices encountered in deep learning models), among others, or any combination thereof. The processor(s) 1720 may be coupled directly or indirectly to one or more computer-readable storage media (e.g., memory) 1730. The memory 1730 may include random access memory (RAM), read-only memory (ROM), disk drive, tape drive, etc., or any combinations thereof. The memory 1730 may be configured to store programs and data, including data structures. In some embodiments, the memory 1730 may also include a frame buffer for storing data arrays.

In some embodiments, another system may assume the data analysis, image processing, or other functions of the processor(s) 1720. In response to commands received from an input device, the programs or data stored in the memory 1730 may be archived in long term storage or may be further processed by the processor and presented on the display 1740.

In some embodiments, the disclosed methods (e.g., FIGS. 1, 3, 7, 10, and 13) may be implemented using software applications that are stored in a memory and executed by the one or more processors (e.g., CPU and/or GPU). In some embodiments, the disclosed methods may be implemented using software applications that are stored in memories and executed by one or more processors distributed across the system.

As such, any of the modules of the system 1700 may be a general-purpose computer system, that becomes a specific purpose computer system when executing the routines and methods of the disclosure. The systems and/or modules of the system 1700 may also include an operating system and micro instruction code. The various processes and functions described herein may either be part of the micro instruction code or part of the application program or routine (or any combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIG. 17. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

The disclosures of each and every publication cited herein are hereby incorporated herein by reference in their entirety.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for correcting MR data comprising:
providing an inhomogeneity field/response map of a region of interest;
wherein the inhomogeneity field/response map is a high-resolution $B_0$ inhomogeneity field/response map;
providing MR data of the region of interest;
wherein the MR data is CEST Z-spectrum image(s)/spectrum or MT Z-spectrum image(s)/spectrum, each voxel of the MR data corresponds to a plurality of subvoxels of the $B_0$ inhomogeneity field/response map;
registering the inhomogeneity field/response map and the MR data;
constructing a subvoxel discrete $B_0$ response from the registered inhomogeneity field/response map;
constructing a voxel discrete Z-spectrum;
determining an intravoxel inhomogeneity correction coefficient for each voxel of at least one subregion of the region of the interest using the inhomogeneity field/response map;
wherein the determining the intravoxel inhomogeneity correction co-efficient includes deconvolving the subvoxel discrete $B_0$ response from the voxel discrete Z-spectrum; and
correcting each voxel of the MR data of the region of interest using the intravoxel inhomogeneity correction coefficient.

2. The method according to claim 1, wherein the subvoxel discrete $B_0$ response is represented by a subvoxel discrete $B_0$ point spread function (PSF).

3. A method for correcting MR data comprising:
providing an inhomogeneity field/response map of a region of interest;
wherein the inhomogeneity field/response map is a high-resolution $B_0$ inhomogeneity field/response map;
providing MR data of the region of interest;
wherein the MR data is MR spectroscopy (MRS)/MR spectroscopic imaging (MRSI) image(s)/spectrum; and
wherein each voxel of the MRS/MRSI image(s)/spectrum corresponds to a plurality of subvoxels of the $B_0$ inhomogeneity field/response map; and
registering the inhomogeneity field/response map and the MR data;
constructing a subvoxel discrete $B_0$ response from the registered $B_0$ inhomogeneity field/response map, and constructing the MRS/MRSI image(s)/spectrum using an interval that is equal to the subvoxel discrete $B_0$ response;
determining an intravoxel inhomogeneity correction coefficient for each voxel of at least one subregion of the region of the interest using the inhomogeneity field/response map;
wherein the determining the intravoxel inhomogeneity correction co-efficient includes deconvolving the subvoxel discrete $B_0$ response from the voxel discrete MRS/MRSI spectrum; and
correcting each voxel of the MR data of the region of interest using the intravoxel inhomogeneity correction coefficient.

4. The method according to claim 3, wherein:
the constructing the MRS/MRSI image(s)/spectrum includes constructing MR real signals, MR imaginary signals, complex signal, MRS signal with a phase adjustment, and/or a combination thereof; and
the deconvolving includes deconvolving the MR real signals, the MR imaginary signals, the complex signal, the MRS signal with the phase adjustment, and/or a combination thereof.

5. The method according to claim 4, wherein the deconvolving the MR real signals and the MR imaginary signals are performed independently, and the method further comprising:
integrating the MR real signals and the MR imaginary signals after the deconvolving to reconstruct complex MRS signal.

6. The method according to claim 3, wherein the subvoxel discrete $B_0$ response is represented by a subvoxel discrete $B_0$ point spread function.

7. A method for correcting MR data:
providing an inhomogeneity field/response map of a region of interest;
wherein the inhomogeneity field/response map is a high-resolution $B_0$ inhomogeneity field/response map;
providing MR data of the region of interest;
wherein the MR data is CEST non Z-spectrum image(s)/spectrum or MT non Z-spectrum image(s)/spectrum;
registering the inhomogeneity field/response map and the MR data;
determining a voxel inhomogeneity correction coefficient for each voxel of at least one subregion of the region of the interest using the registered $B_0$ inhomogeneity field/response map and the MR data; and correcting each voxel of the MR data of the region of interest using the voxel inhomogeneity correction coefficient;

wherein the corrected data is corrected using the intravoxel inhomogeneity correction coefficient.

8. The method according to claim 7, wherein the determining the voxel inhomogeneity correction coefficient includes determining a regression of $B_0$ inhomogeneity and measured CEST effect of one or more subregions of the region of interest using the registered $B_0$ inhomogeneity field/response map and the MR data, the one or more subregions of the region of interest having a homogenous CEST signal intensity.

9. A method for correcting MR data comprising:

providing an inhomogeneity field/response map of a region of interest;

providing MR data of the region of interest;

determining an intravoxel inhomogeneity correction coefficient for each voxel of at least one subregion of the region of the interest using the inhomogeneity field/response map; and correcting each voxel of the MR image(s)/spectrum of the region of interest using the intravoxel inhomogeneity correction coefficient;

determining a quasi-steady state signal for each voxel for each saturation offset using the corrected voxel, T1 map, B1, and scan parameters, the scan parameters including saturation time; and standardizing each corrected voxel using the quasi-steady state signal for each saturation offset.

10. The method according to claim 9, wherein the determining the quasi-steady state spectrum for each voxel includes:

determining a steady state spinlock relaxation rate using at least the saturation time; and determining the quasi-steady state signal for each voxel for each saturation offset based on the steady state spinlock relaxation rate.

11. The method according to claim 9, further comprising:

determining one or more quantitative measurements using each standardized and/or corrected voxel for each offset.

12. A method for correcting MR data comprising providing a $B_0$ inhomogeneity field map/response of a region of interest;

providing MR data of the region of interest, the MR data corresponding to CEST data or MT data;

registering the $B_0$ inhomogeneity field/response map and the MR data;

determining a voxel inhomogeneity correction coefficient for each voxel of at least one subregion of the region of the interest using the registered $B_0$ inhomogeneity field/response map;

correcting each voxel of the MR data of the region of interest using the voxel inhomogeneity correction coefficient;

determining a quasi-steady state signal for each voxel for each saturation offset using the corrected voxel, T1 map, B1, and scan parameters, the scan parameters including saturation time; and standardizing each corrected voxel using the quasi-steady state signal for each saturation offset.

13. The method according to claim 12, wherein the determining the quasi-steady state spectrum for each voxel includes:

determining a steady state spinlock relaxation rate using-using at least the saturation time; and determining the quasi-steady state signal for each voxel for each saturation offset based on the steady state spinlock relaxation rate.

14. The method according to claim 12, further comprising:

determining one or more quantitative measurements using each standardized and/or corrected voxel.

15. The method according to claim 13, the CEST data is non Z-spectrum data and the MT data is non Z spectrum data.

16. The method according to claim 1, further comprising:

determining one or more quantitative measurements using each standardized and/or corrected voxel for each offset.

17. The method according to claim 3, further comprising:

determining one or more quantitative measurements using each standardized and/or corrected voxel for each offset.

18. The method according to claim 7, further comprising:

determining one or more quantitative measurements using each standardized and/or corrected voxel for each offset.

19. The method according to claim 13, further comprising:

determining one or more quantitative measurements using each standardized and/or corrected voxel for each offset.

* * * * *